US010744279B2

(12) United States Patent
Tabata et al.

(10) Patent No.: US 10,744,279 B2
(45) Date of Patent: Aug. 18, 2020

(54) ULTRASONIC NEBULIZER

(71) Applicant: OMRON HEALTHCARE CO., LTD., Muko-shi, Kyoto (JP)

(72) Inventors: Makoto Tabata, Kyoto (JP); Takaaki Okanishi, Kyoto (JP); Shigeo Kinoshita, Kyoto (JP)

(73) Assignee: OMRON HEALTHCARE CO., LTD., Tokyo (JP)

( * ) Notice: Subject to any disclaimer, the term of this patent is extended or adjusted under 35 U.S.C. 154(b) by 497 days.

(21) Appl. No.: 15/698,514

(22) Filed: Sep. 7, 2017

(65) Prior Publication Data
US 2017/0368271 A1 Dec. 28, 2017

Related U.S. Application Data

(63) Continuation of application No. PCT/JP2016/050865, filed on Jan. 13, 2016.

(30) Foreign Application Priority Data

Mar. 25, 2015 (JP) .................. 2015-063261

(51) Int. Cl.
| A61M 11/00 | (2006.01) |
| A61M 15/00 | (2006.01) |
| B05B 17/06 | (2006.01) |
| B05B 7/00 | (2006.01) |
| A61M 16/16 | (2006.01) |
| B05B 12/08 | (2006.01) |

(52) U.S. Cl.
CPC ...... *A61M 11/005* (2013.01); *A61M 15/0085* (2013.01); *A61M 16/162* (2013.01);
(Continued)

(58) Field of Classification Search
CPC .... A61M 16/14; A61M 16/16; A61M 16/108; A61M 11/00; A61M 11/005;
(Continued)

(56) References Cited

U.S. PATENT DOCUMENTS 5,881,714 A * 3/1999 Yokoi .................. A61M 11/005
128/200.14
6,152,383 A * 11/2000 Chen ................... B05B 17/0615
128/200.16
(Continued)

FOREIGN PATENT DOCUMENTS

CN 102355915 A 2/2012
JP S56-118762 U 9/1981
(Continued)

OTHER PUBLICATIONS

Sep. 3, 2019 Office Action issued in Chinese Patent Application No. 201680010684.0.
(Continued)

*Primary Examiner* — Samchuan C Yao
*Assistant Examiner* — Margaret M Luarca
(74) *Attorney, Agent, or Firm* — Oliff PLC

(57) ABSTRACT

An ultrasonic nebulizer includes: a working tank in which an ultrasonic vibrator is incorporated and in which a working liquid is stored facing the ultrasonic vibrator; a medicine tank that stores a medicinal liquid, at least a bottom portion thereof being dipped in the working liquid; and a main body that includes an oscillation circuit that is to drive the ultrasonic vibrator. The medicine tank is configured to be detachable with respect to the working tank. The working tank is configured to be detachable with respect to the main body.

6 Claims, 10 Drawing Sheets

(52) U.S. Cl.
CPC ........ *B05B 7/0012* (2013.01); *B05B 17/0615* (2013.01); *A61M 2205/123* (2013.01); *A61M 2205/14* (2013.01); *A61M 2205/276* (2013.01); *A61M 2205/3317* (2013.01); *A61M 2205/3386* (2013.01); *A61M 2205/3606* (2013.01); *A61M 2205/50* (2013.01); *A61M 2205/502* (2013.01); *A61M 2209/10* (2013.01); *B05B 12/081* (2013.01)

(58) Field of Classification Search
CPC ............... A61M 11/0085; B05B 17/06; B05B 17/0615; B05B 17/0607; F24F 6/00
See application file for complete search history.

(56) References Cited

U.S. PATENT DOCUMENTS

| | | | |
|---|---|---|---|
| 6,283,118 B1* | 9/2001 | Lu | ........................ A61M 11/005 128/200.16 |
| 2003/0146224 A1* | 8/2003 | Fujii | ..................... A47J 41/022 220/592.27 |

FOREIGN PATENT DOCUMENTS

| | | |
|---|---|---|
| JP | S60-23023 Y2 | 7/1985 |
| JP | H04-099255 U | 8/1992 |
| JP | H05-137786 A | 6/1993 |
| JP | H05-070668 U | 9/1993 |
| JP | H06-241912 A | 9/1994 |
| JP | 2004-121605 A | 4/2004 |
| JP | 2005-278742 A | 10/2005 |
| JP | 2006-217955 A | 8/2006 |
| WO | 2010/106834 A1 | 9/2010 |

OTHER PUBLICATIONS

Apr. 5, 2016 International Search Report issued in International Patent Application No. PCT/JP2016/050865.

Jan. 15, 2019 Office Action issued in Japanese Patent Application No. 2015-063261.

* cited by examiner

ULTRASONIC NEBULIZER

TECHNICAL FIELD

This invention relates to an ultrasonic nebulizer. More specifically, this invention relates to an ultrasonic nebulizer that transmits ultrasonic vibration generated by an ultrasonic vibrator to a medicine tank via a working liquid in a working tank and thereby atomizes a medicinal liquid in the medicine tank.

BACKGROUND ART

Conventionally, as this type of ultrasonic nebulizer, there is known to be an ultrasonic nebulizer that includes an atomizer that is configured to be detachable with respect to a main body, as disclosed in Patent Document 1 (JP 2005-278742A), for example. A power converter that converts AC power from a power source cord, a control circuit that outputs a control signal, and the like are installed in the main body, and an external connection terminal (contact electrode) that is to be connected to the atomizer is provided on the main body. The atomizer contains a storage portion that stores liquid to be atomized (medicinal liquid), a storage portion that stores a transmission liquid (working liquid), an ultrasonic wave generator, and a power source unit. If the atomizer is mounted on the main body, the outputs of the power converter and the control circuit in the main body are supplied to the power source unit of the mounted atomizer via the external connection terminal. During use, in the atomizer, the ultrasonic waves from the ultrasonic wave generator are transmitted to the liquid to be atomized via the transmission liquid, and the liquid to be atomized is atomized.

CITATION LIST

Patent Literature

Patent Document 1: JP 2005-278742A

SUMMARY OF INVENTION

Technical Problem

Incidentally, from a hygienic viewpoint such as preventing the risk of infection, it is preferable that a working tank storing a working liquid is periodically washed with washing liquid, and/or disinfected with a disinfecting liquid. In particular, it is advantageous if the working tank can be left immersed in the disinfecting liquid, since no labor is required.

However, Patent Document 1 (JP 2005-278742A) does not disclose any contrivance regarding washing and/or disinfecting the storage portion (working tank) storing the transmission liquid (working liquid). For this reason, it is inferred that a large amount of labor will be required in order to wash and/or disinfect the storage portion (working tank).

In view of this, it is an object of the present invention to provide an ultrasonic nebulizer according to which a user (a doctor, nurse, or the like) can easily wash and/or disinfect a working tank.

Solution to the Problem

In order to solve the foregoing problems, an ultrasonic nebulizer of the present invention includes:

a working tank in which an ultrasonic vibrator is incorporated and in which a working liquid is stored facing the ultrasonic vibrator;

a medicine tank that stores a medicinal liquid, at least a bottom portion thereof being dipped in the working liquid; and a main body that includes an oscillation circuit that is to drive the ultrasonic vibrator, wherein the medicine tank is configured to be detachable with respect to the working tank, and the working tank is configured to be detachable with respect to the main body.

In the present specification, the "working liquid" need only be a medium through which ultrasonic vibration can be transmitted, and water is typically used thereas. Examples of the medicinal liquid are not particularly limited and include a saline solution or a liquid mixture of a saline solution and Bisolvon.

Also, the medicine tank being configured to be "detachable" with respect to the working tank means that the medicine tank has a form in which the medicine tank can be mounted on the working tank and the medicine tank has a form in which the medicine tank can be removed from the working tank.

Similarly, the working tank being "configured to be detachable" with respect to the main body means that the shapes of the main body and the working tank are shapes according to which the working tank can be mounted on the main body and the working tank can be removed from the main body.

With the ultrasonic nebulizer of the present invention, the output of the oscillation circuit is applied from the main body to the ultrasonic vibrator in a state in which at least the bottom portion of the medicine tank is dipped in the working liquid in the working tank. Accordingly, ultrasonic vibration generated by the ultrasonic vibrator is transmitted to the medicine tank via the working liquid in the working tank, and the medicinal liquid in the medicine tank is atomized.

As described above, from a hygienic viewpoint such as preventing the risk of infection, it is desirable to periodically wash and/or disinfect the working tank that stores the working liquid. In view of this, in the ultrasonic nebulizer of this invention, the medicine tank is configured to be detachable with respect to the working tank, and the working tank is configured to be detachable with respect to the main body. Accordingly, in a state in which the working tank and the medicine tank are mounted on the main body, the user (a doctor, nurse, or the like) can easily take out only the working tank by first removing the working tank along with the medicine tank from the main body, and then removing the medicine tank from the working tank, for example. Alternatively, in a state in which the working tank and the medicine tank are mounted on the main body, the user can easily take out only the working tank by first removing the medicine tank from the working tank, and then removing the working tank from the main body. Accordingly, it is possible to easily wash and/or disinfect the working tank separately. The medicine tank can also be easily cleaned and/or disinfected separately.

Note that it is desirable that the main body-side contact electrode that emits the output of the oscillation circuit is provided on the main body, the tank-side contact electrode that is connected to the electrode of the ultrasonic vibrator is provided on the working tank, and in the state in which the working tank is mounted on the main body, the output of the oscillation circuit is applied to the ultrasonic vibrator through the main body-side contact electrode and the tank-side contact electrode.

Also, it is desirable to use a configuration in which mounting is performed by bringing the working tank close to the main body from a certain direction, and conversely, removal is performed by separating the working tank from the main body in that direction.

In particular, it is desirable to use a configuration in which mounting is performed by bringing the working tank close to the main body from above, and conversely, removal is performed by separating the working tank from the main body in the upward direction. Thus, the main body is placed on a platform such as a desk, and mounting is easily performed if a user holds only the working tank (or the medicine tank instead) with a hand and brings it close to the main body.

Also, it is desirable that the main body includes a containing portion that surrounds and contains the working tank and the medicine tank. Thus, in a state in which the working tank and the medicine tank are mounted on the main body, the working tank and the medicine tank are protected by being surrounded by the main body, and the working tank and the medicine tank no longer unexpectedly detach from the main body.

With an ultrasonic nebulizer of an embodiment, the working tank has a specific gravity that is larger overall compared to that of water or a disinfecting liquid.

In the present specification, the "disinfecting liquid" indicates a disinfecting liquid (e.g., an aqueous solution of sodium hypochlorite) that is to be used to disinfect the working tank.

With the ultrasonic nebulizer of this embodiment, the working tank has a specific gravity that is larger overall than that of water or the disinfecting liquid. Accordingly, once the user immerses the working tank in the disinfecting liquid in an orientation of being open upward in order to disinfect the working tank, the working tank maintains the state of having sunk in the disinfecting liquid with its own weight. In other words, no situation occurs in which the working tank floats and a portion (the bottom portion, etc.) of the working tank is exposed at the liquid surface. As a result, it is sufficient that the user leaves the working tank immersed in the disinfecting liquid in order to disinfect the working tank. Accordingly, hardly any labor is required.

With an ultrasonic nebulizer of an embodiment, the working tank includes an approximately tube-shaped outer circumferential wall and an outer bottom surface that closes a lower portion of the outer circumferential wall, and the working tank has a center of gravity at a portion that is closer to the bottom surface portion than a center of buoyancy is, the center of buoyancy being a location at which a buoyant force is received from water or disinfecting liquid when the working tank is immersed in the water or the disinfecting liquid.

With the ultrasonic nebulizer of this embodiment, in the process of sinking in the water or the disinfecting liquid, the working tank will upright itself by receiving a rotational moment caused by a buoyant force received at the center of buoyancy and a gravitational force received at the center of gravity. Accordingly, the working tank can enter a state of being upright on the bottom surface of the disinfecting liquid tank, and can receive the disinfecting liquid in a preferable state.

In the present specification, the "lower portion" of the outer circumferential wall indicates the lower portion when the working tank is in its original orientation of being open upward. The working tank being "upright" means being in the original orientation in which the outer bottom surface is oriented downward and the working tank is open upward.

According to another aspect, an ultrasonic nebulizer includes:

a working tank in which an ultrasonic vibrator is incorporated and in which a working liquid is stored facing the ultrasonic vibrator;

a medicine tank that stores a medicinal liquid, at least a bottom portion thereof being dipped in the working liquid; and a main body that includes an oscillation circuit that is to drive the ultrasonic vibrator, wherein the medicine tank is configured to be detachable with respect to the working tank, the working tank is configured to be detachable with respect to the main body, the working tank includes an approximately tube-shaped outer circumferential wall and an outer bottom surface that closes a lower portion of the outer circumferential wall, a bottom portion of the working tank has a double-bottomed structure that includes the outer bottom surface and an inner bottom surface that is provided on the outer bottom surface via a gap, and the working tank has a specific gravity that is larger overall compared to that of water or a disinfecting liquid and a weight is provided in the gap so that the working tank has a center of gravity at a part that is closer to the outer bottom surface than a center of buoyancy is, the center of buoyancy being a location at which a buoyant force is received from the water or the disinfecting liquid when the working tank is immersed in the water or the disinfecting liquid.

The "weight" means a member or material (e.g., metal, resin, etc.) with a specific gravity greater than 1.

With the ultrasonic nebulizer of this aspect, the weight is provided in the gap so that the working tank has the center of gravity at a part that is closer to the outer bottom surface than the center of buoyancy is. Accordingly, it is possible to achieve a structure in which the center of gravity is included at a part that is closer to the outer bottom surface than the center of buoyancy is, the center of buoyancy being a location at which the buoyant force is received from the water or disinfecting liquid when the working tank is immersed in the water or disinfecting liquid.

Note that it is desirable that the ultrasonic vibrator is incorporated in the gap that forms the double-bottomed structure of the working tank.

With an ultrasonic nebulizer of an embodiment, the weight is composed of a sealing material that fills the gap.

With the ultrasonic nebulizer of this embodiment, the weight is composed of a sealing material that fills the gap. That is, the sealing material functions as the weight, and functions to seal and protect a member arranged in the gap (e.g., a wire that connects to the electrode of the ultrasonic vibrator, etc.).

According to yet another aspect, an ultrasonic nebulizer of the present invention includes:

a working tank in which an ultrasonic vibrator is incorporated and in which a working liquid is stored facing the ultrasonic vibrator;

a medicine tank that stores a medicinal liquid, at least a bottom portion thereof being dipped in the working liquid; and a main body that includes an oscillation circuit that is to drive the ultrasonic vibrator, wherein the medicine tank is configured to be detachable with respect to the working tank, a configuration is used in which the working tank is mounted on the main body by being brought close thereto from above, and conversely, the working tank is removed from the main body by being separated therefrom in an upward direction, and the main body includes a cylindrical containing portion that opens upward and surrounds and contains the mounted working tank and medicine tank.

Accordingly, in the state in which the working tank and the medicine tank are mounted on the main body, the working tank and the medicine tank are protected by being surrounded by the main body, and the working tank and the medicine tank are not likely to unintentionally separate from the main body.

With an ultrasonic nebulizer of an embodiment, an opening that is continuous with the containing portion is provided on a rear surface side of a main portion of the main body that surrounds the working tank and the medicine tank, a carrying handle is integrally attached to an outer circumferential wall of the working tank, and in a state in which the working tank is mounted on the main body, the handle is arranged at the opening that is continuous with the containing portion of the main body.

With the ultrasonic nebulizer of this embodiment, the direction of the working tank is fixed with respect to the main body. Accordingly, the direction of a member (e.g., an air duct of the medicine tank cover) attached above the working tank is fixed with respect to the main body.

With an ultrasonic nebulizer of an embodiment, a dimension in a left-right direction of the opening is set to be a dimension large enough for a first to be inserted therein.

With the ultrasonic nebulizer of this embodiment, it is easy to mount the working tank on the main body in a state in which a person grasps the handle with a hand.

With an ultrasonic nebulizer of an embodiment, in a state in which the working tank is mounted on the main body, a rear surface of the handle matches a rear surface of the main body.

With the ultrasonic nebulizer of this embodiment, in the state in which the working tank and the medicine tank are mounted on the main body, the working tank and the medicine tank are protected by being surrounded by the main body, and the working tank and the medicine tank are not likely to unintentionally separate from the main body.

Advantageous Effects of the Invention

As is evident from the above description, with the ultrasonic nebulizer of this invention, the user can easily wash and/or disinfect the working tank.

DESCRIPTION OF EMBODIMENTS

Hereinafter, embodiments of the present invention will be described in detail with reference to the drawings.

Figure 1:
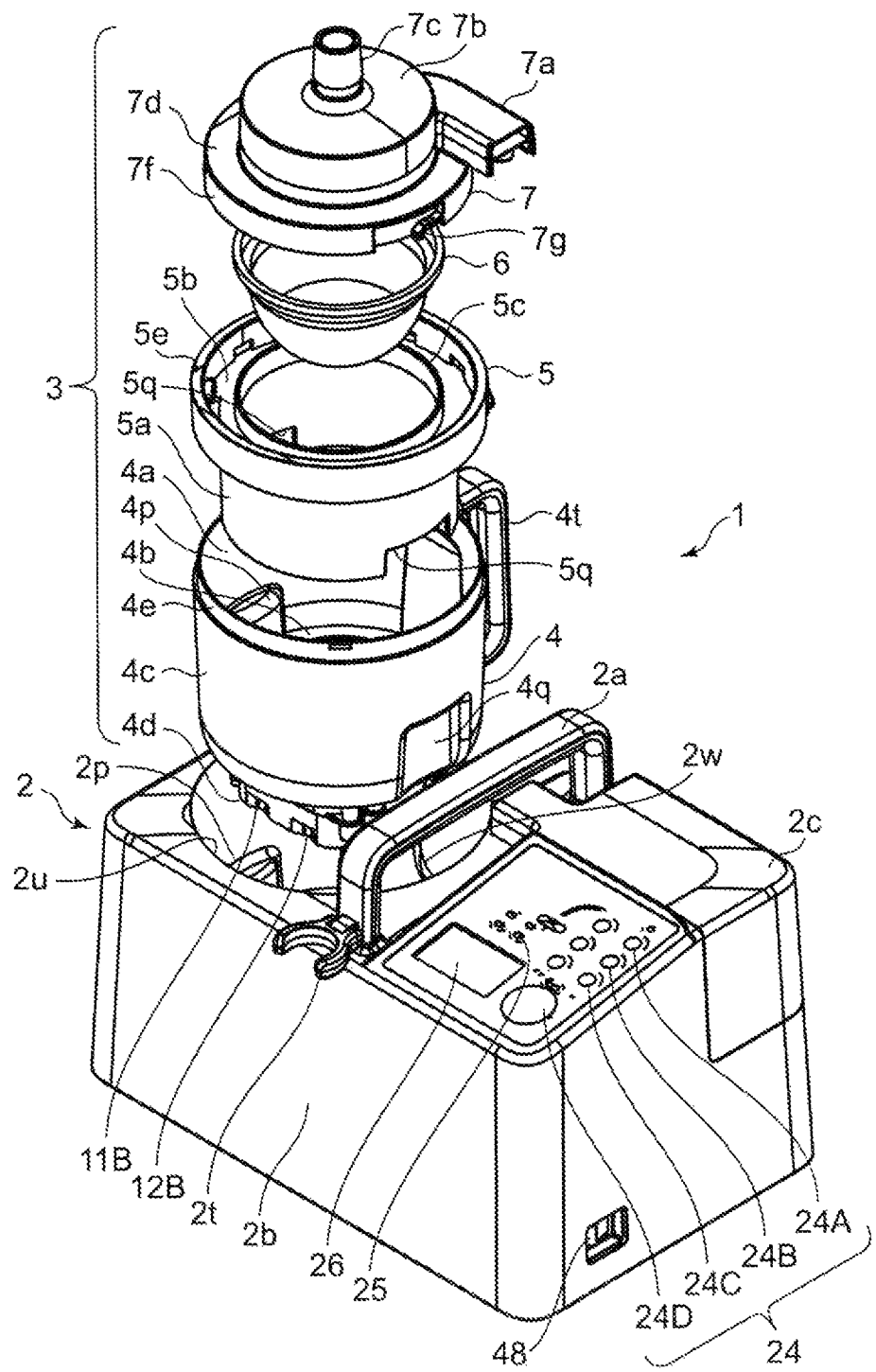
FIG. 1 is a diagram showing an exploded view from above and obliquely to the right of an ultrasonic nebulizer of an embodiment of the invention.
Figure 2:
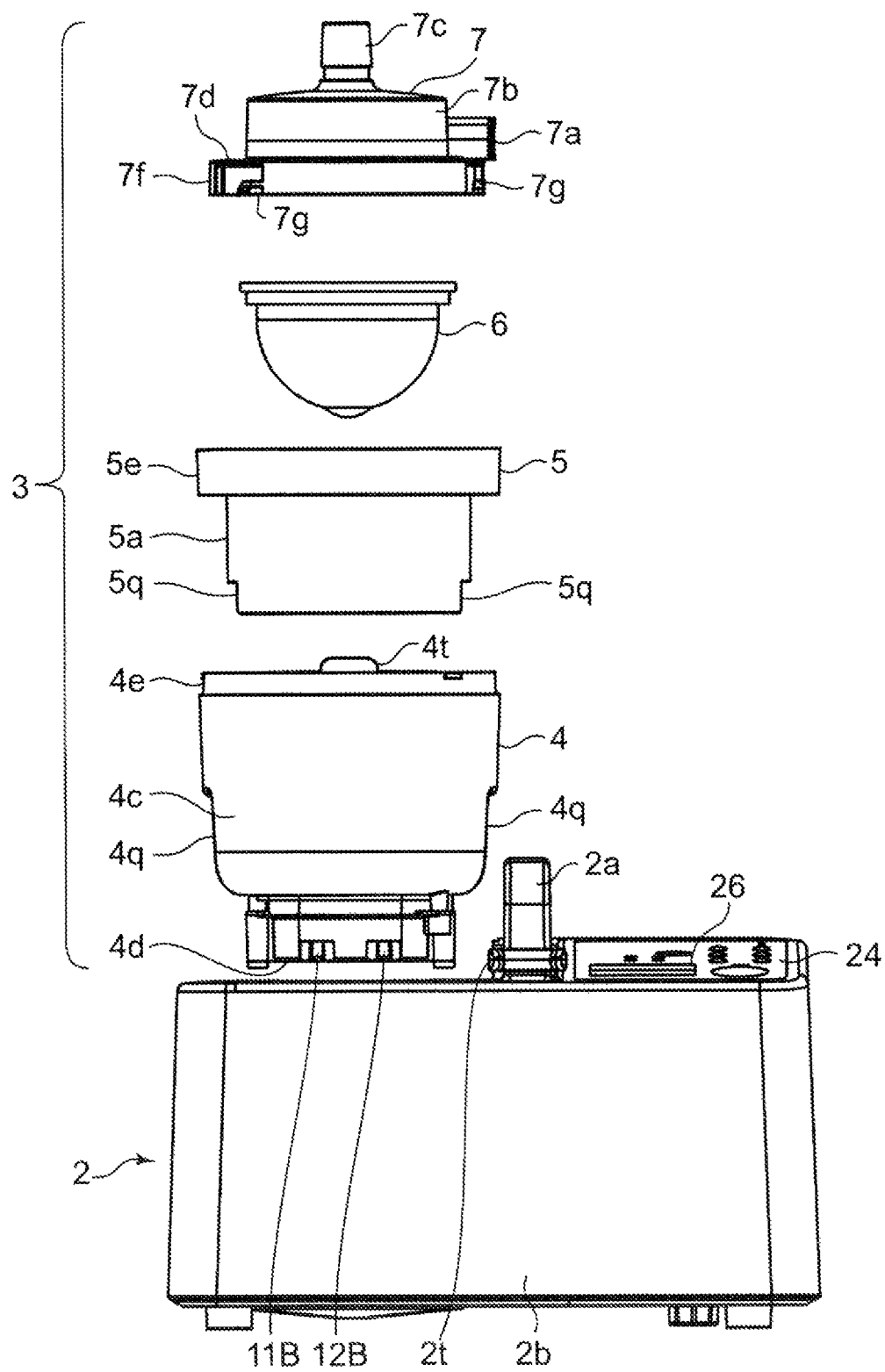
FIG. 2 is a diagram showing a view from the front of the ultrasonic nebulizer shown in FIG. 1.

FIG. 1 shows an exploded view from above and obliquely to the right of an ultrasonic nebulizer (indicated overall by reference numeral 1) of an embodiment of the invention. FIG. 2 shows a view from the front of the ultrasonic nebulizer 1 shown in FIG. 1.

As can be understood from FIGS. 1 and 2, the ultrasonic nebulizer 1 generally includes a main body 2 and a tank unit 3 that is configured to be detachable with respect to the main body 2.

The tank unit 3 includes a working tank 4, a medicine tank support 5, a medicine tank 6, and a medicine tank cover 7. The elements 4, 5, 6, and 7 of the tank unit 3 can be assembled by being overlaid in the stated order in a fit-together manner by the hand of a person without need for a tool, and can be disassembled in the inverse order.

The main body 2 includes a main portion 2*b* that forms a housing, and a carrying handle 2*a* that is provided on the upper surface of the main portion 2*b* and extends in the front-rear direction. An approximately cylindrical containing portion 2*u* for surrounding and containing the tank unit 3 is provided in the left half of the main portion 2*b* (leftward of the handle 2*a*). An opening 2*w* that is continuous with the containing portion 2*u* is provided on the rear surface side of the main portion 2*b*. The width (dimension in the left-right direction) of the opening 2*w* is set to be a dimension large enough that a person's fist can be inserted therein, for the sake of convenience in mounting the tank unit 3. A seating platform portion 2*d* (see FIGS. 3 and 4) on which the tank unit 3 is to be mounted is provided at the bottom of the containing portion 2*u* (below the main portion 2*b*). As shown in FIGS. 1 and 2, a C-shaped hose holder 2*t* for holding the leading end portion of an air suction hose 8 (see FIG. 9) attached to the medicine tank cover 7 is provided on the front portion of the handle 2*a*.

An operation switch portion 24, an LED (light-emitting diode) display unit 25, and an LCD (liquid crystal display element) display unit 26 are provided on the right half of the upper surface of the main body 2 (rightward of the handle 2*a*). The operation switch portion 24 includes a timer adjustment key switch 24A by which the user (a doctor, a nurse, or the like) inputs a continuous spray time, an air flow adjustment key switch 24B, which serves as a first operation portion and is for inputting an air flow setting value, an atomization amount adjustment key switch 24C, which serves as a second operation portion and is for inputting an atomization amount setting value, and a spraying start/stop switch 24D for instructing the start or stopping of spraying. Note that the key switches 24A, 24B, and 24C each include an up key and a down key (indicated by the left and right pairs of circular marks in FIGS. 1 and 2) for increasing and reducing the input values. The LED display unit 25 and the LCD display unit 26 receive and display signals indicating the atomization amount, the air flow, the timer, the start of spraying, and states such as error from the later-described CPU 28 (see FIG. 9).

As shown in FIG. 1, a power switch 48 for the ultrasonic nebulizer 1 is provided on the right-side surface of the main body 2. Also, an air cover 2c that covers a later-described air fan is provided on the right rear portion of the main body 2.

Figure 5:
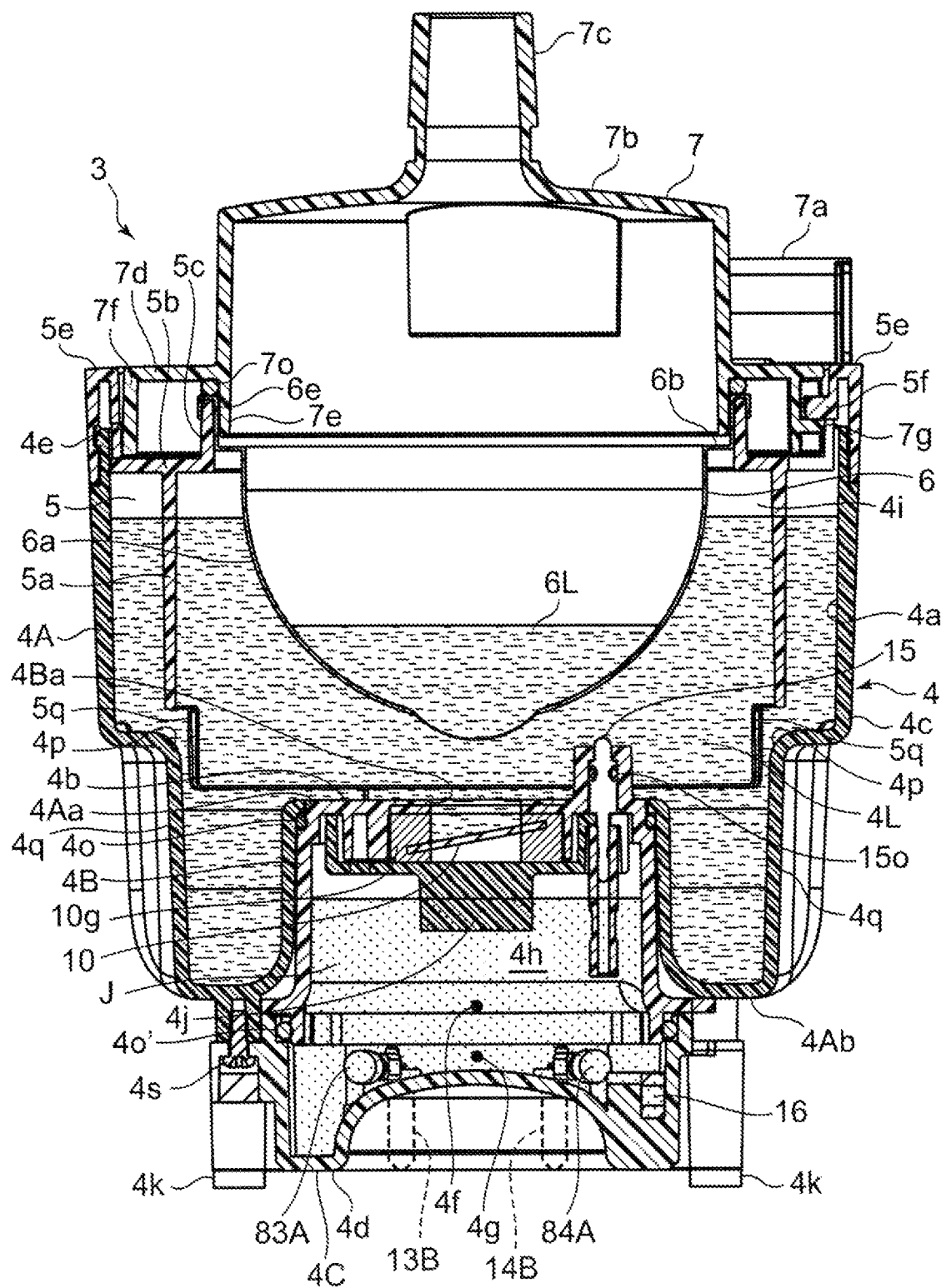
FIG. 5 is a longitudinal cross-sectional view (a cross-sectional view parallel to the surface of the page in FIG. 2) showing a configuration of the tank unit included in the ultrasonic nebulizer.
Figure 6:
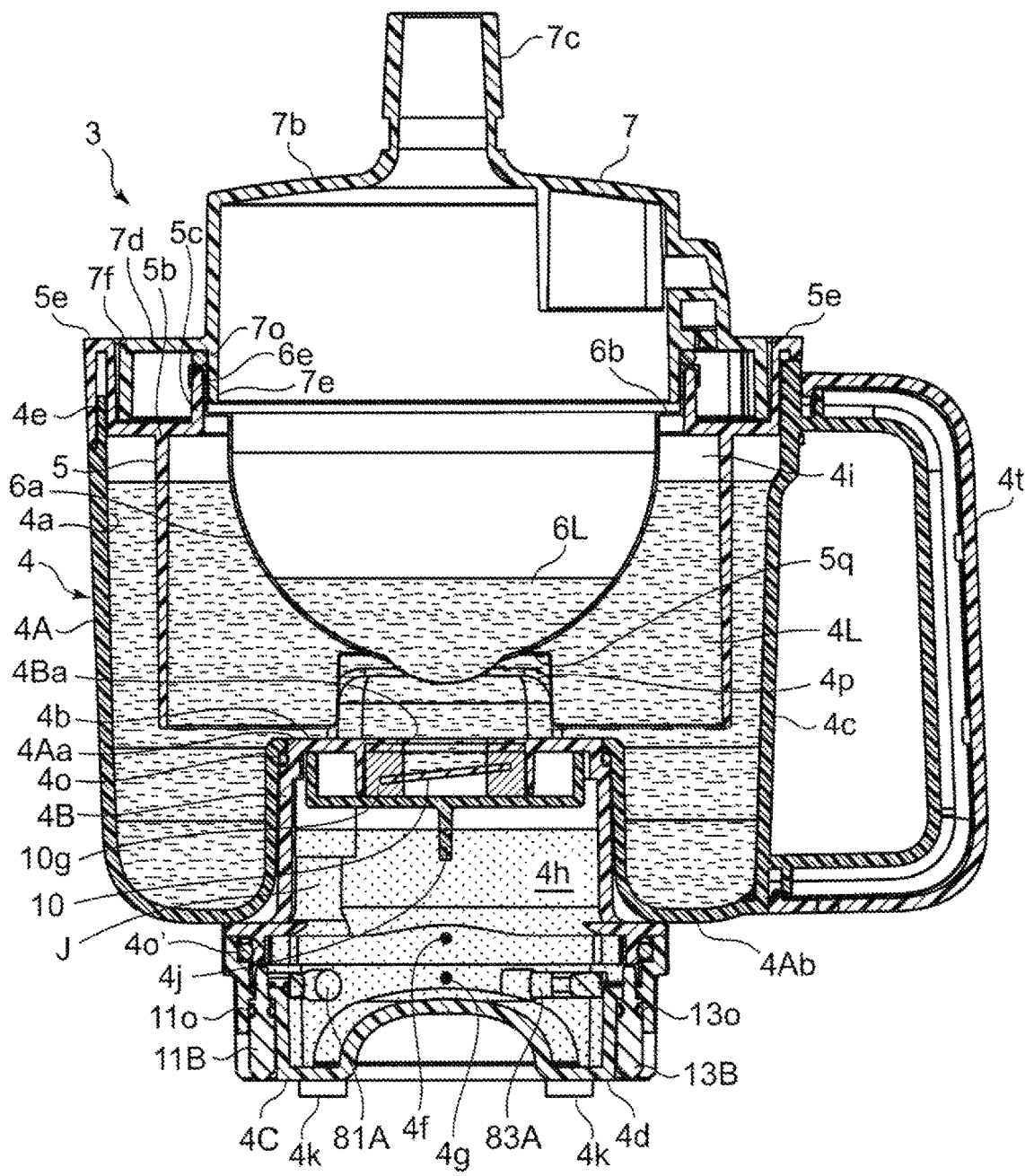
FIG. 6 is another longitudinal cross-sectional view (a cross-sectional view orthogonal to the surface of the page in FIG. 2) showing the configuration of the tank unit.

FIG. 5 shows a longitudinal cross section taken parallel to the page surface of FIG. 2, of the tank unit 3, which is in an assembled state. FIG. 6 shows a longitudinal cross section taken perpendicular to the page surface of FIG. 2, of the tank unit 3 in such a state.

As can be understood from FIGS. 5 and 6, the working tank 4 is open upward and includes: an approximately cylindrical inner circumferential wall 4a; an inner bottom surface 4b that covers the lower portion of the inner circumferential wall 4a; an approximately cylindrical outer circumferential wall 4c that wraps around the inner circumferential wall 4a; an outer bottom surface 4d that covers the lower portion of the outer circumferential wall 4c; a top portion 4e that connects the upper edge of the inner circumferential wall 4a and the upper edge of the outer circumferential wall 4c; and a carrying handle 4t that is integrally attached to the outer circumferential wall 4c. A working liquid (in this example, water) 4L is contained in a tank inner space 4i, which is formed by the inner circumferential wall 4a and the inner bottom surface 4b, which constitute the inner surface of the working tank 4. A gap 4h is provided between the inner bottom surface 4b and the outer bottom surface 4d. Accordingly, the working tank 4 has a double-bottomed structure.

More specifically, the working tank 4 is constituted by a first member 4A composed of ABS (acrylonitrile butadiene styrene copolymer) resin, which forms the inner circumferential wall 4a and the outer circumferential wall 4c, a second member 4B composed of PPS (polyphenylene sulfide) resin, which forms the inner bottom surface 4b, and a third member 4C composed of PPS resin, which forms the outer bottom surface 4d. The first member 4A has an approximately cylindrical shape, has a lower portion 4Ab that is curved so as to protrude downward, and has an approximately circular opening 4Aa that is formed in a rising manner on the inner side. The second member 4B has an approximately cylindrical shape and the upper portion thereof fits watertightly into the opening 4Aa of the first member 4A via an O ring 4o. The upper portion of the second member 4B forms the inner bottom surface 4b of the working tank 4. An opening 4Ba is formed in the inner bottom surface 4b of the working tank 4 (second member 4B). The third member 4C has an approximately square tube-shaped outer shape and the upper portion thereof is fit watertightly around the lower portion of the second member 4B via an O ring 4o'. The lower portion of the third member 4C is closed and forms the outer bottom surface 4d of the working tank 4. The third member 4C is attached to the lower portion 4Ab of the first member 4A using multiple screws 4s (only one is shown in FIG. 5). As a result, the working tank 4 is integrally assembled in a state in which the second member 4B is interposed between the first member 4A and the third member 4C. Note that legs 4k of the working tank 4 are provided in a downwardly-projecting manner on the outer bottom surface 4d (third member 4C).

A plate-shaped ultrasonic vibrator 10 is incorporated in the gap 4h that forms the double-bottomed structure of the working tank 4. The vibrating surface of the ultrasonic vibrator 10 is arranged so as to face the tank inner space 4i from below the inner bottom surface 4b, through the opening 4Ba provided in the inner bottom surface 4b. More specifically, the ultrasonic vibrator 10 is held by being fit in a frame-shaped rubber holder 10g. The rubber holder 10g is pressed onto the periphery of the opening 4Ba of the inner bottom surface 4b from below by a pressing member 4j that is attached by a screw (not shown) to the inner bottom surface 4b. Accordingly, together with the holder 10g, the ultrasonic vibrator 10 is incorporated in a state in which the working liquid 4L does not leak from the tank inner space 4i through the opening 4Ba.

Also, a liquid level sensor 15 for detecting the liquid surface of the working liquid 4L is arranged at a predetermined height level of the tank inner space 4i. The liquid level sensor 15 generates a voltage signal that indicates whether or not the liquid level of the working liquid 4L in the working tank 4 exceeds the height level (necessary level). The liquid level sensor 15 is attached watertightly with an O ring 15o, penetrating through the inner bottom surface 4b. Furthermore, a magnet 16 that is to be used to detect whether or not the working tank 4 has been mounted on the main body 2 is incorporated in the gap 4h.

Figure 9:
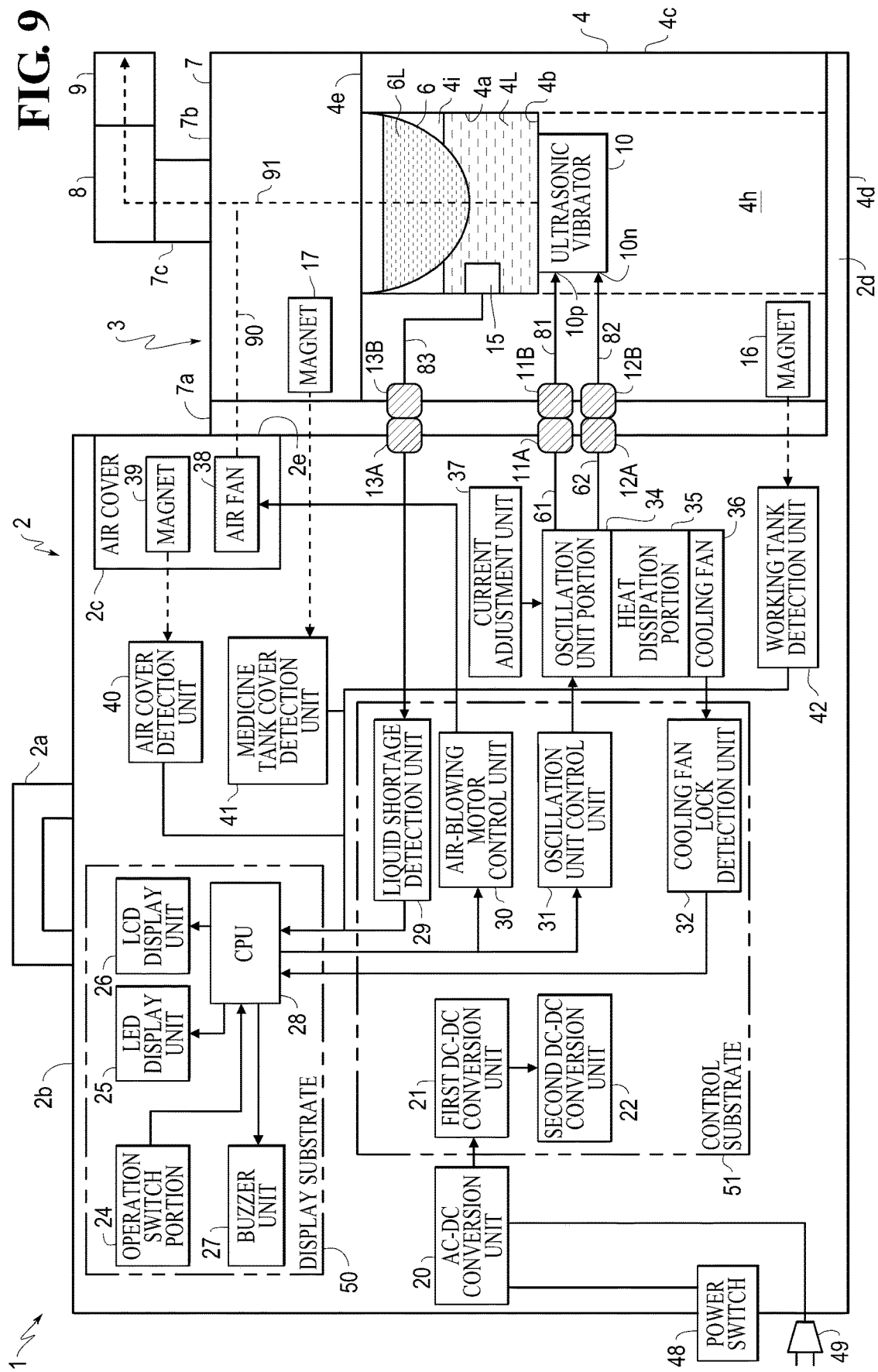
FIG. 9 is a diagram showing a schematic block configuration of the ultrasonic nebulizer.

In this example, first, second, third, and fourth tank-side contact electrodes 11B, 12B, 13B, and 14B are provided on the bottom portion (third member 4C) of the working tank 4 so as to penetrate through the outer wall (FIGS. 1 and 2 show the first and second tank-side contact electrodes 11B and 12B on the front surface side of the working tank 4, FIG. 5 shows the third and fourth tank-side contact electrodes 13B and 14B on the rear surface side of the working tank 4, and FIG. 6 shows the first and third tank-side contact electrodes 11B and 13B). The tank-side contact electrodes 11B, 12B, 13B, and 14B are attached watertightly to the outer wall with O rings (FIG. 6 shows O rings 11o and 13o that correspond to the first and third tank-side contact electrodes 11B and 13B). As shown in FIG. 9, the first and second tank-side contact electrodes 11B and 12B are connected to first and second electrodes 10p and 10n of the ultrasonic vibrator 10 by wires 81 and 82, respectively. Also, the third tank-side contact electrode 13B is connected to the liquid level sensor 15 by a wire 83. Note that metal members 81A and 83A in FIGS. 5 and 6 form portions of the wires 81 and 83. A metal member 84A is connected to a fourth tank-side contact electrode (dummy tank-side contact electrode) 14B.

Also, in this example, as a weight, a sealing material J with a specific gravity of 1.2 to 1.6 (in this example, a specific gravity of 1.2) fills a gap 4h that forms the double-bottomed structure of the working tank 4, so as to occupy the space from the lower portion to the height level near the ultrasonic vibrator 10. A urethane-based resin is used as the sealing material J, for example. The sealing material J functions as a weight, and functions to seal and protect a member arranged in the gap 4h (e.g., a wire that connects to the electrode of the ultrasonic vibrator 10, etc.). Note that since the sealing material J does not reach the height of the ultrasonic vibrator 10, it does not have an adverse effect on the vibration of the ultrasonic vibrator 10.

A first member 4A that forms the working tank 4 is composed of ABS resin as described above, and the specific gravity thereof is about 1.1. A second member 4B and a third member 4C are composed of PPS resin, and the specific gravities thereof are about 1.3. The inner-side portion (side facing the outer circumferential wall 4c) of the handle 4t is composed of ABS resin that is integral with the first member 4A, and the specific gravity thereof is about 1.1. The outer-side portion of the handle 4t is composed of PPS resin, and the specific gravity thereof is about 1.3. The sealing material J is provided as a weight so as to occupy most of the gap 4h, and as a result, the working tank 4 has an overall weight of about 530 g, an overall volume (volume excluding the tank inner space 4i) of about 470 cm$^3$, and an overall specific gravity of about 1.13. That is, the working tank 4 has a specific gravity that is larger overall compared to that of water (which has a specific gravity of 1) or the disinfecting liquid (e.g., the aqueous solution of sodium hypochlorite, which has a specific gravity of less than 1.1), which is to be used to disinfect the working tank.

Also, the center of gravity 4g of the working tank 4 is at a part that is closer to the outer bottom surface 4d than the center of buoyancy 4f is, the center of buoyancy 4f being a location at which the buoyant force is received from the water or disinfecting liquid when the working tank 4 is immersed in the water or disinfecting liquid.

Note that as shown in FIGS. 1 and 2 as well as FIGS. 5 and 6, with the working tank 4, specific locations (a left and right pair of locations in a view from the front) are curved toward the tank interior with respect to the circumferential direction of the first member 4A. Accordingly, a left and right pair of recesses 4q and 4q are formed in the outer circumferential wall 4c. Also, a left and right pair of protrusions 4p and 4p are formed in the inner circumferential wall 4a. The recesses 4q and 4q are used to guide the tank unit 3 (working tank 4) when the tank unit 3 (working tank 4) is mounted on the main body 2 (main portion 2b). The protrusions 4p and 4p are used to fix the orientation (direction) of the medicine tank support 5 with respect to the working tank 4.

As shown in FIGS. 1 and 2 as well as FIGS. 5 and 6, the medicine tank support 5 includes: a cylindrical portion 5a that is contained in the tank inner space 4i of the working tank 4, a flat support portion 5b that is provided along the upper end of the cylindrical portion 5a, an engagement portion 5e that is provided along the outer edge of the support portion 5b and opens downward with a C-shaped cross-section, and a projection portion 5c that is provided along the inner edge of the support portion 5b and projects upward. Cut-outs 5q and 5q that open downward in C shapes are formed at specific locations (a left and right pair of locations in a view from the front) with respect to the circumferential direction of the cylindrical portion 5a. As shown in FIGS. 5 and 6, the medicine tank support 5 is arranged overlaid on the working tank 4 from above due to the engagement portion 5e fitting into the top portion 4e of the working tank 4. At this time, the orientation (direction) of the medicine tank support 5 is fixed with respect to the working tank 4 by matching the cut-outs 5q with the projections 4p of the working tank 4. Conversely, if the medicine tank support 5 is pulled upward off of the working tank 4, the medicine tank support 5 is removed from the working tank 4. Note that in the medicine tank support 5, a projection 5f for locking the medicine tank cover 7 is provided at a specific location with respect to the circumferential direction on the inner side of the engaging portions 5e.

The medicine tank 6 includes a main portion 6a that is formed so as to protrude downward in an approximate hemispherical shape, a flat step portion 6b that is provided along the upper end of the main portion 6a, and an engagement portion 6e that is provided along the outer edge of the step portion 6b and opens downward with a C-shaped cross-section. Due to the engagement portion 6e fitting onto the projection portion 5c of the medicine tank support 5, the medicine tank 6 is arranged overlaid on the medicine tank support 5 from above. Conversely, if the medicine tank 6 is pulled upward off of the medicine tank support 5, the medicine tank 6 is removed from the medicine tank support 5. A medicinal liquid 6L that is to be atomized is contained in the medicine tank 6. Examples of the medicinal liquid 6L include a saline solution or a liquid mixture of a saline solution and Bisolvon. When the tank unit 3 is assembled, the bottom portion of the medicine tank 6 is dipped in the working liquid 4L in the working tank 4.

Figure 7:
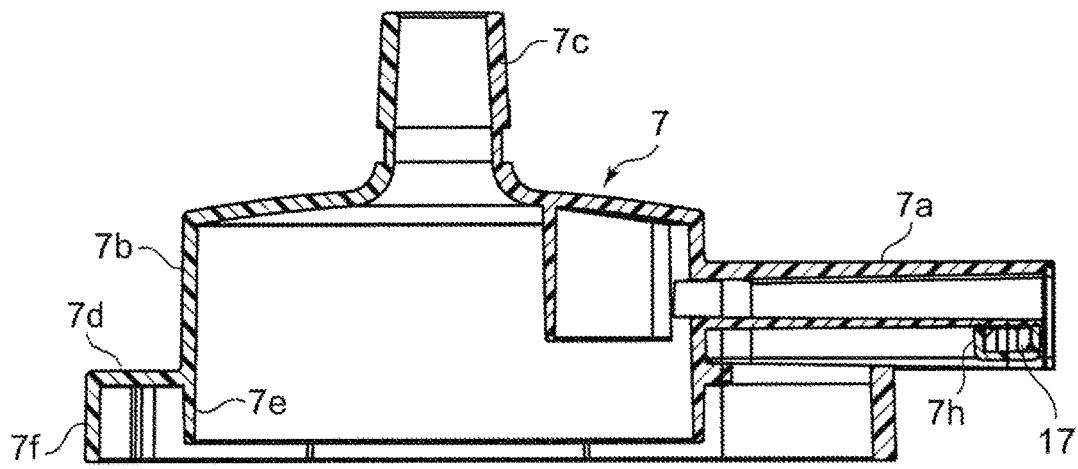
FIG. 7 is a cross-sectional view showing a configuration of a medicine tank cover included in the tank unit.

As shown in FIGS. 5 and 6, as well as in FIG. 7, which shows only the medicine tank cover 7, the medicine tank cover 7 includes: a simple cylindrical cover portion 7b with an upper portion that is closed so as to cover the upper portion of the medicine tank 6; an air duct 7a that is in communication with the cover portion 7b and extends laterally; and an emission port 7c that is in communication with the cover portion 7b and extends upward. Also, a flat flange portion 7d is formed along the periphery of the cover portion 7b. Furthermore, a ring-shaped outer edge portion 7f that projects downward is formed along the outer edge of the flange portion 7d. As shown in FIG. 7, together with a magnet attachment case 7h, a magnet 17 that is to be used to detect whether or not the medicine tank cover 7 has been mounted correctly on the main body 2 is incorporated on the lower portion of the entrance to the air duct 7a.

As shown in FIGS. 1, 2, and 5, an engagement portion 7g that is to be locked on the engagement portion 5e of the medicine tank support 5 is formed at a specific location with respect to the circumferential direction of the outer edge portion 7f on the medicine tank cover 7. As shown in FIGS. 5 and 6, the medicine tank cover 7 is arranged overlaid on the medicine tank 6 from above in a state in which an O ring 7o is attached around a lower portion 7e of the cover portion 7b. More specifically, the engagement portion 6e of the medicine tank 6 is pressed from above by the medicine tank cover 7 via the O ring 7o. Along with this, the engagement portion 7g is locked by passing below the projection 5f of the medicine tank support 5 due to the medicine tank cover 7 being rotated (in this example, clockwise in a view from above) slightly about the center (in the perpendicular direction) of the cover portion 7b. Accordingly, the medicine tank cover 7 is attached to the medicine tank support 5 in a mode in which the engagement portion 6e of the medicine tank 6 is interposed between the medicine tank cover 7 and the projecting portion 5c of the medicine tank support 5 via the O ring 7o, and the air duct 7a of the medicine tank cover 7 is arranged in a predetermined orientation (direction) with respect to the working tank 4 (the handle 4t of the working tank 4). In this example, in a view directly facing the handle 4t of the working tank 4, the entrance of the air duct 7a of the medicine tank cover 7 is arranged so as to face leftward. Conversely, if the medicine tank cover 7 is rotated slightly counterclockwise about the center of the cover portion 7b and the medicine tank cover 7 is pulled upward, the medicine tank cover 7 is removed.

Figure 3:
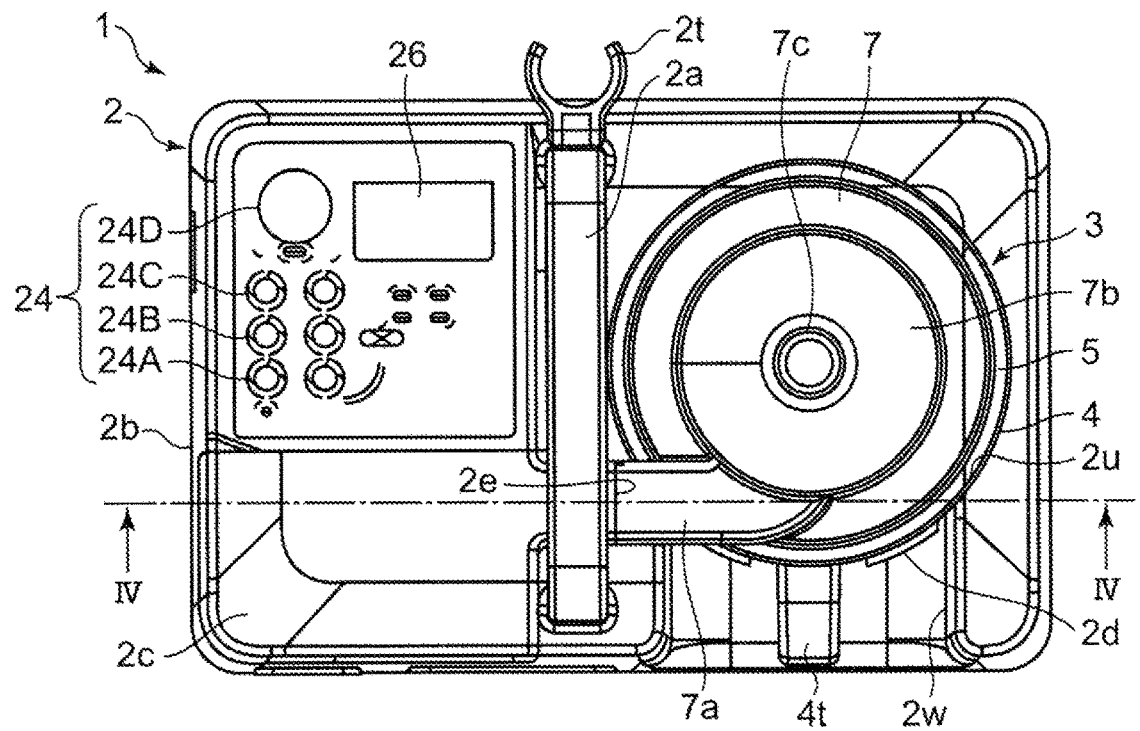
FIG. 3 is a diagram showing a view from above of the ultrasonic nebulizer in a tank unit mounted state.

FIG. 3 shows a view from above of a state (tank unit mounted state) in which the tank unit 3 is mounted on the main body 2 (the front surface of the main body 2 is drawn above, and the rear surface is drawn below). Also, FIG. 4 shows a cross-sectional view taken along line IV-IV in FIG. 3 and viewed in the direction of the arrows.

Figure 4:
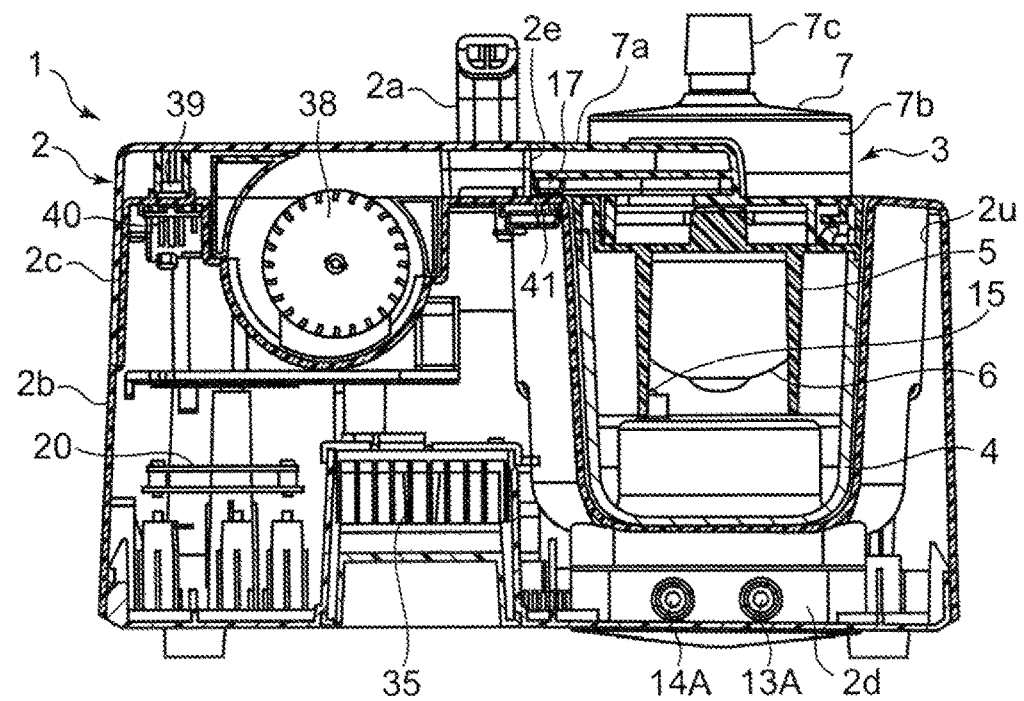
FIG. 4 is a diagram showing a cross-sectional view taken along line IV-IV in FIG. 3 and viewed in the direction of the arrows.

As shown in FIGS. 3 and 4, in the tank unit mounted state, the tank unit 3 is attached on the seating platform portion 2d on the bottom of the containing portion 2u of the main body 2. The tank unit 3 is attached in a mode in which the handle 4t of the working tank 4 faces rearward of the main body 2 and the outer side of the handle 4t approximately matches the rear surface of the main body 2. An arrangement is used in which the entrance of the air duct 7a of the medicine tank cover 7 extends above the main body 2 (main portion 2b). In the tank unit mounted state, the tank unit 3 is protected by being surrounded by the main body 2, and the tank unit 3 (particularly, the working tank 4) no longer detaches unexpectedly from the main body 2.

As shown in FIG. 4, an air fan (includes a motor that rotates the fan) 38 for blowing air to the medicine tank 6 is arranged on the upper portion of the main body 2 (main portion 2b). The air fan 38 is covered by an air cover 2c that can be detached from the main portion 2b. A vent 2e that communicates with the air duct 7a on the tank unit 3 side in the tank unit mounted state is provided in the air cover 2c. In the main portion 2b, a medicine tank cover detection unit 41 is provided at a location that corresponds to directly below the magnet 17 of the air duct 7a. The medicine tank cover detection unit 41 includes a hole IC (integrated circuit including a magnetic sensor) and uses the magnetic force of the magnet 17 incorporated in the medicine tank cover 7 to detect whether or not the medicine tank cover 7 has been correctly mounted on the main portion 2b (whether or not the air duct 7a matches the vent 2e).

Also, a magnet 39 that is used to detect whether or not the air cover 2c has been mounted on the main portion 2b is attached to the inner side of the air cover 2c. In the main portion 2b, the air cover detection unit 40 is provided at a location that corresponds to directly below the magnet 39 of the air cover 2c. The air cover detection unit 40 includes a hole IC and uses the magnetic force of the magnet 39 attached to the air cover 2c to detect whether or not the air cover 2c has been mounted on the main portion 2b.

A later-described AC-DC conversion unit 20 and a heat dispersion portion 35 are arranged in the lower portion in the main portion 2b.

Figure 8:
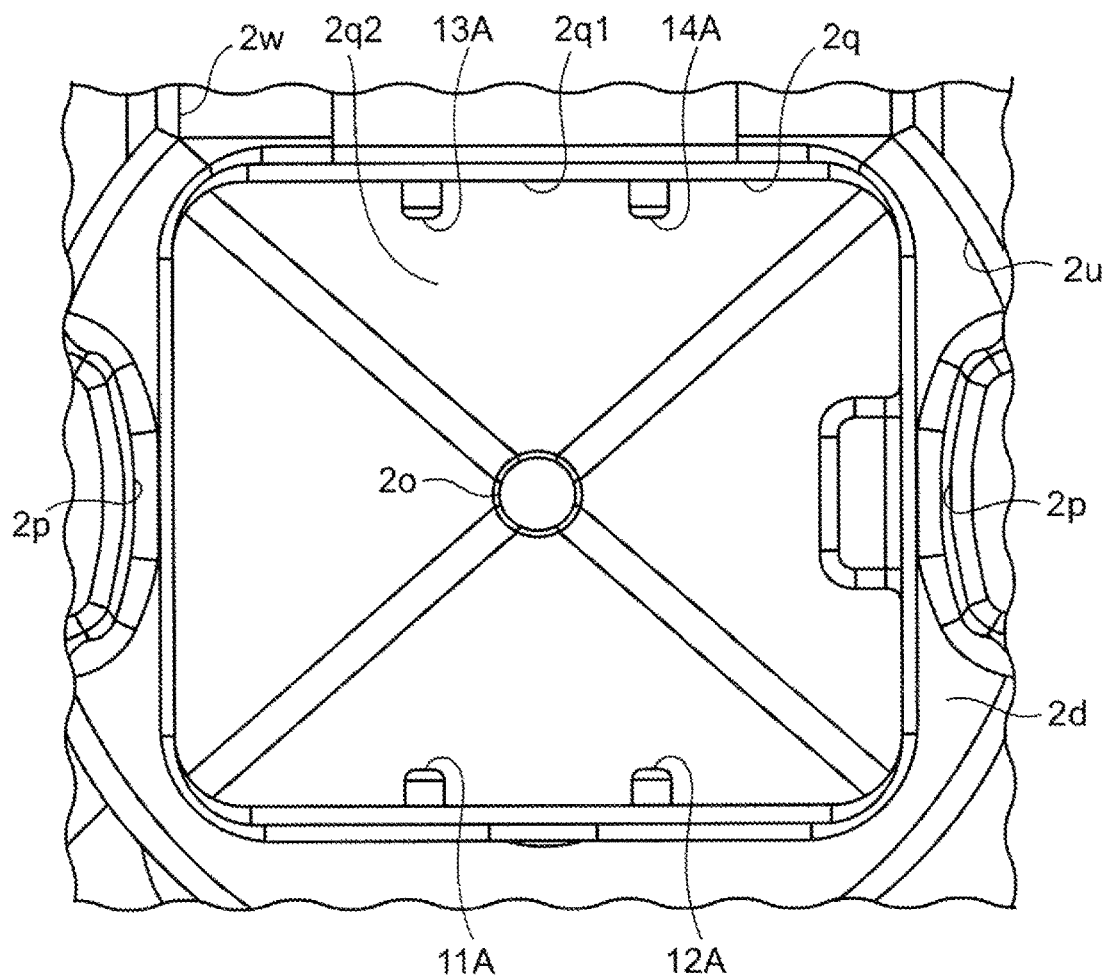
FIG. 8 is a diagram showing a view from above of a containing portion for containing the tank unit in the main body of the ultrasonic nebulizer.

FIG. 8 shows a view from above of the containing portion 2u for containing the tank unit 3 in the main body 2 (the front surface side of the main body 2 is drawn below and the rear surface side is drawn above). The protrusions 2p and 2p that are to be fit into the recesses 4q and 4q (see FIGS. 1 and 2) of the working tank 4 are formed at specific locations (a left and right pair of locations in a view from the front) with respect to the circumferential direction of the inner surface of the containing portion 2u. Approximately rectangular recesses 2q are formed on the seating platform portion 2d at the bottom of the containing portion 2u and the first, second, third, and fourth main body-side contact electrodes 11A, 12A, 13A, and 14A are provided so as to protrude from side walls 2q1 of the recesses 2q. The first, second, third, and fourth main body-side contact electrodes 11A, 12A, 13A, and 14A are biased in an orientation of protruding from the side walls 2q1 due to coil springs (not shown). Note that in the unlikely event that the working liquid 4L or the like is spilled, a bottom wall 2q2 of the recess 2q inclines so as to gradually become lower toward the center, and a liquid discharge port 2o is provided in the center of the bottom wall 2q2.

The working tank 4 (or the tank unit 3; the same follows hereinafter in this paragraph) is mounted on the seating platform portion 2d in the containing portion 2u of the main body 2 shown in FIG. 8 by being lowered from above in a standing orientation. At this time, the recesses 4q and 4q (see FIGS. 2 and 5) of the working tank 4 fit over the protrusions 2p and 2p on the inner surface of the containing portion 2u, and the working tank 4 is guided in a horizontal plane. Also, the orientation (direction) of the working tank 4 is fixed with respect to the main body 2 due to the approximately square tube-shaped bottom portion (third member 4C) of the working tank 4 being fit into the recess 2q of the seating platform portion 2d (note that the orientation of the working tank 4 with respect to the main body 2 is roughly fixed using the orientation of the handle 4t of the working tank 4). The first, second, third, and fourth main body-side contact electrodes 11A, 12A, 13A, and 14A come into contact with and connect to the first, second, third, and fourth tank-side contact electrodes 11B, 12B, 13B, and 14B of the working tank 4 respectively when the working tank 4 is lowered from above and seated. Conversely, the working tank 4 is removed from the main body 2 by being pulled upward from the seating platform portion 2d of the main body 2.

Thus, with the ultrasonic nebulizer 1, the working tank 4 is configured to be detachable with respect to the main body 2. Also, as stated above, the medicine tank 6 and the medicine tank cover 7 are configured to be detachable with respect to the working tank 4 via the medicine tank support 5. Accordingly, the user (a doctor, a nurse, or the like) can easily take out only the working tank 4 by first removing the tank unit 3 (includes the working tank 4, the medicine tank support 5, the medicine tank 6, and the medicine tank cover 7) from the main body 2 in the tank unit mounted state, and then removing the medicine tank cover 7, the medicine tank 6, and the medicine tank support 5 in the stated order from the working tank 4 of the tank unit 3. Alternatively, it is possible to easily take out only the working tank 4 by first removing the medicine tank 6 and the medicine tank cover 7 from the medicine tank support 5 in the tank unit mounted state, then removing the medicine tank support 5 from the working tank 4, and furthermore removing the working tank 4 from the main body 2. Accordingly, the working tank 4 can be easily cleaned and/or disinfected separately. Also, the medicine tank cover 7, the medicine tank 6, and the medicine tank support 5 can each be easily cleaned and/or disinfected with a disinfecting liquid separately.

FIG. 9 schematically shows a schematic block configuration of the ultrasonic nebulizer 1 (which is in the tank unit mounted state). Note that in FIG. 9, for the sake of simplicity, the medicine tank support 5, the fourth main body-side contact electrode 14A, and the fourth tank-side contact electrode 14B are not shown.

The main body 2 (main portion 2b) is provided with the above-described power switch 48, an AC (alternating current) plug 49, the AC-DC conversion unit 20, a display substrate 50, a control circuit 51, an oscillation unit portion 34, a heat dissipation portion 35 and cooling fan 36 that are arranged along the oscillation unit portion 34, a current adjustment unit 37, the air cover detection unit 40, the medicine tank cover detection unit 41, and the working tank detection unit 42. In addition to the above-described operation switch portion 24, LED (light-emitting diode) display unit 25, and LCD (liquid crystal display element) display unit 26, the display substrate 50 is provided with a buzzer portion 27 and a CPU 28 that controls the overall operation of the ultrasonic nebulizer 1. The control substrate 51 is provided with a first DC-DC conversion unit 21, a second DC-DC conversion unit 22, a liquid shortage detection unit 29, an air-blowing motor control unit 30, an oscillation unit control unit 31, and a cooling fan lock detection unit 32.

The AC plug 49 is connected to a commercially-available AC power source (in this example, AC 100V). The power switch 48 is used to switch on and off the overall power of the ultrasonic nebulizer 1.

The AC-DC conversion unit 20 converts the AC 100V from the commercial AC power source into DC 48V. The DC 48V is used as a power source for causing the oscillation unit portion 34 and the ultrasonic vibrator 10 to operate.

The first DC-DC conversion unit 21 steps down the DC 48V to DC 12V. The DC 12V is used as a power source for causing the air cover detection unit 40, the air fan 38, and the cooling fan 36 to operate.

The second DC-DC conversion unit 22 steps down the DC 12V to DC 5V. The DC 5V is used mainly as system power to cause elements 24 to 28 on the display substrate 50 to operate.

As described above, the operation switch portion 24 is provided in order for a user (a doctor, a nurse, or the like) to perform switch input of an atomization amount, air flow, a timer, the start of spraying, and the like. The operation switch portion 24 transmits the switch input to the CPU 28.

Also, the LED display unit 25 and the LCD display unit 26 receive and display signals indicating the atomization amount, the air flow, the timer, the start of spraying, and states such as error from the CPU 28.

The buzzer portion 27 receives a signal indicating the end of a timer or a state such as error from the CPU 28 and performs notification using sound.

The liquid shortage detection unit 29 receives the voltage signal output from the liquid level sensor 15 in the tank unit mounted state and transmits a detection signal indicating whether or not the working liquid 4L in the working tank 4 has been filled to a necessary level to the CPU 28.

The air-blowing motor control unit 30 receives a PWM (pulse width modulation) signal for controlling the rotation rate of the air fan 38 from the CPU 28 and drives the air fan 38 according to the PWM signal.

In this example, the air fan 38 includes a sirocco fan, and a motor that rotates the sirocco fan at a rotation rate that corresponds to the PWM signal from the air-blowing motor control unit 30. The air fan 38 that is driven performs air-blowing 90 through the vent 2e to the tank unit 3 side.

The oscillation unit control unit 31 receives a PWM signal for controlling the atomization amount performed by the ultrasonic vibrator 10 from the CPU 28 and transmits it to the oscillation unit portion 34.

In this example, the oscillation unit portion 34 includes a Colpitts oscillation circuit, receives a PWM signal for driving the ultrasonic vibrator 10 from the oscillation unit control unit 31, generates an oscillation waveform (AC oscillation potential) based on the PWM signal, and outputs the oscillation waveform to the ultrasonic vibrator 10.

In this example, the heat dissipation portion 35 is composed of a metal plate (copper plate, etc.) that has fins. The heat dissipation portion 35 emits heat transmitted from the oscillation unit portion 34 to the outside of the main body 2 using wind from the cooling fan 36.

The current adjustment portion 37 adjusts the current that the oscillation unit portion 34 allows to flow to the ultrasonic vibrator 10.

The cooling fan lock detection unit 32 receives a voltage signal (this will be called a "cooling fan lock signal") that is generated when the cooling fan 36 stops (locks) and converts it to a voltage level that can be input to the CPU 28. The voltage-converted cooling fan lock signal is input to the CPU 28. If the cooling fan locks, the CPU 28 performs control for displaying an error stating that the cooling fan 36 has stopped on the LED display unit 25 and the LCD display unit 26 and stopping the spraying operation.

As stated above, the air cover detection unit 40 uses the magnetic force of the magnet 39 attached to the air cover 2c to detect whether or not the air cover 2c has been mounted on the main portion 2b. A detection result indicating whether or not the air cover 2c has been mounted is input to the CPU 28. If the air cover 2c has not been mounted, the CPU 28 performs control for displaying an error stating that the air cover 2c has not been mounted on the LED display unit 25 and the LCD display unit 26 and stopping the spraying operation.

Also, the medicine tank cover detection unit 41 uses the magnetic force of the magnet 17 incorporated in the medicine tank cover 7 to detect whether or not the medicine tank cover 7 has been correctly mounted with respect to the main portion 2b (whether or not the air duct 7a matches the vent 2e). A detection result indicating whether or not the medicine tank cover 7 has been correctly mounted is input to the CPU 28. If the medicine tank cover 7 has not been correctly mounted, the CPU 28 performs control for displaying an error stating that the medicine tank cover 7 has not been correctly mounted on the LED display unit 25 and the LCD display unit 26 and stopping the spraying operation.

In this example, the working tank detection unit 42 includes a hole IC and detects whether or not the working tank 4 has been mounted on the seating platform portion 2b using the magnetic force of the magnet 16 incorporated in the working tank 4. A detection result indicating whether or not the working tank 4 has been mounted is input to the CPU 28. If the working tank 4 has not been mounted, the CPU 28 performs control for displaying an error stating that the working tank 4 has not been mounted on the LED display unit 25 and the LCD display unit 26 and stopping the spraying operation.

In the tank unit mounted state, as described above, the first and second main body-side contact electrodes 11A and 12A come into contact with and are connected to the first and second tank-side contact electrodes 11B and 12B, respectively. At the time of a spraying operation, the output from the oscillation unit portion 34 in the main body 2 is applied to the electrodes 10p and 10n of the ultrasonic vibrator 10 through the first and second main body-side contact electrodes 11A and 12A and the first and second tank-side contact electrodes 11B and 12B. Accordingly, the ultrasonic vibrator 10 in the working tank 4 is driven to generate ultrasonic vibration. The ultrasonic vibration is transmitted to the medicinal liquid 6L in the medicine tank 6 via the working liquid 4L, whereby the medicinal liquid 6L in the medicine tank 6 is atomized. The atomized medicinal liquid (aerosol) 91 is blown by the air-blowing 90 from the air fan 38, and in this example, is supplied to the patient through the suction hose 8 and the mouthpiece 9. Note that instead of the mouthpiece 9, it is possible to include an inhalation mask, a glass nasal olive for inhaling through the nostrils, or the like.

Figure 14:
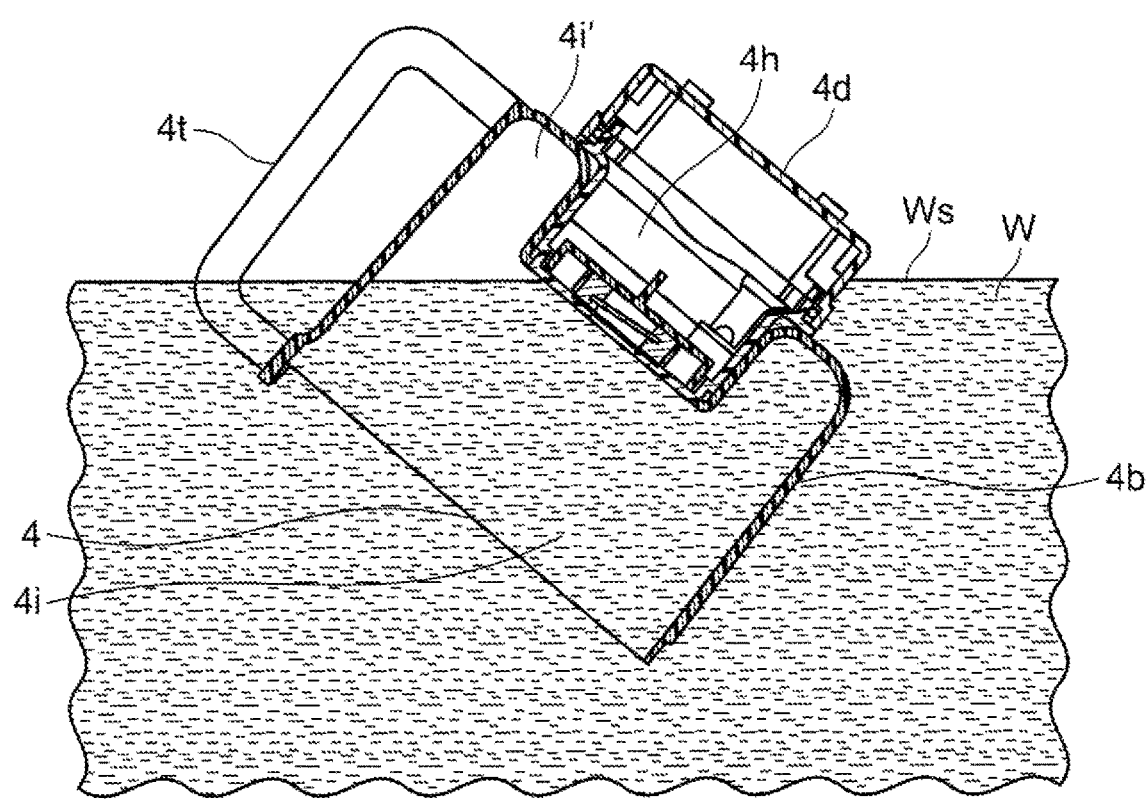
FIG. 14 is a diagram illustrating a problem that can occur in the case where the sealing material has not filled the double-bottomed structure of the working tank.

With the ultrasonic nebulizer 1, as described above, the bottom portion of the working tank 4 has a double-bottomed structure that includes the gap 4h in which the ultrasonic vibrator 10 is incorporated. For this reason, if there is no contrivance (if the gap 4h is left as-is), the bottom portion of the working tank 4 will be relatively light, and as a result, even if the user attempts to immerse the working tank 4 in the disinfecting liquid W in order to disinfect the working tank 4, there is a possibility that the working tank 4 will float in an upside-down orientation and a portion (the bottom portion, etc.) of the working tank 4 will be exposed at the liquid surface Ws, as shown in FIG. 14 for example. In this state, the disinfection of the outer bottom portion 4d and the like of the working tank 4 will be insufficient. Also, if air remains in the portion 4i' that corresponds to the upper portion of the liquid surface Ws in the tank inner space 4i, the disinfection of the portion 4i' will be insufficient.

Figure 10:
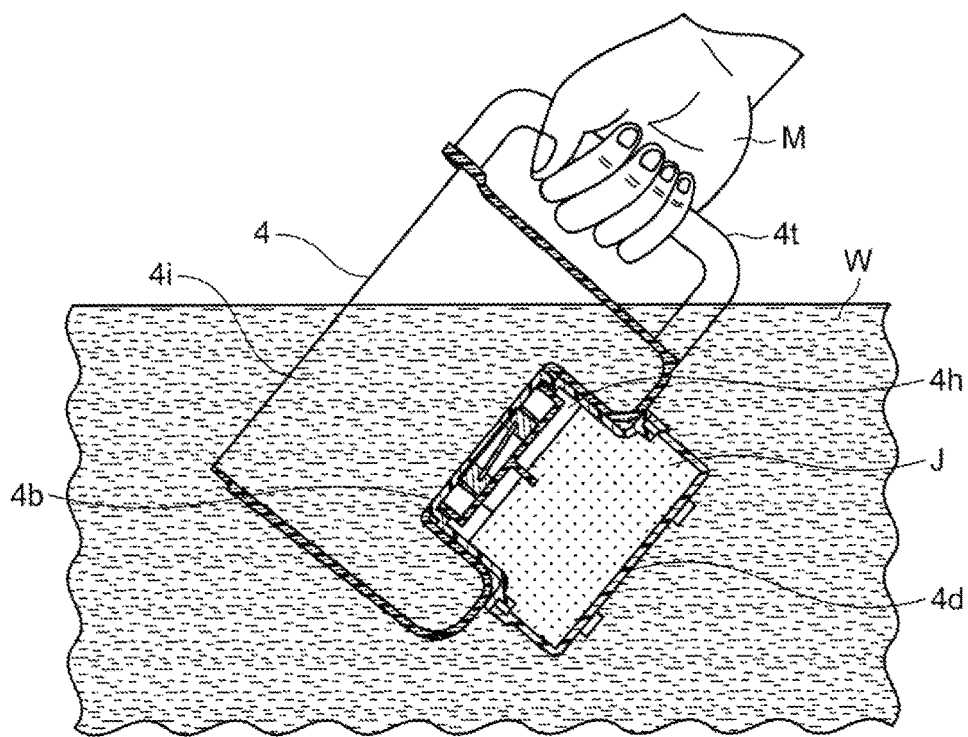
FIG. 10 is a diagram showing a mode in which the working tank included in the tank unit is immersed in disinfecting liquid.

In view of this, in the ultrasonic nebulizer 1, as shown in FIGS. 5 and 6, the sealing material J is provided as a weight so as to occupy the majority of the gap 4h. Accordingly, the working tank 4 has a specific gravity (in this example, about 1.13) that is larger overall compared to that of water or the disinfecting liquid. Accordingly, as shown in FIG. 10, once the user immerses the working tank 4 in the disinfecting liquid W holding the handle 4t with a hand M in order to disinfect the working tank 4 (or more accurately, once the tank inner space 4i is filled with the disinfecting liquid W), the working tank 4 maintains the state of having sunk in the disinfecting liquid W with its own weight. In other words, no situation occurs in which the working tank 4 floats up and a portion (the bottom portion, etc.) of the working tank 4 is exposed at the liquid surface (FIG. 14). As a result, it is sufficient that the user leaves the working tank 4 immersed in the disinfecting liquid W in order to disinfect the working tank 4. Accordingly, hardly any labor is required.

Figure 11:
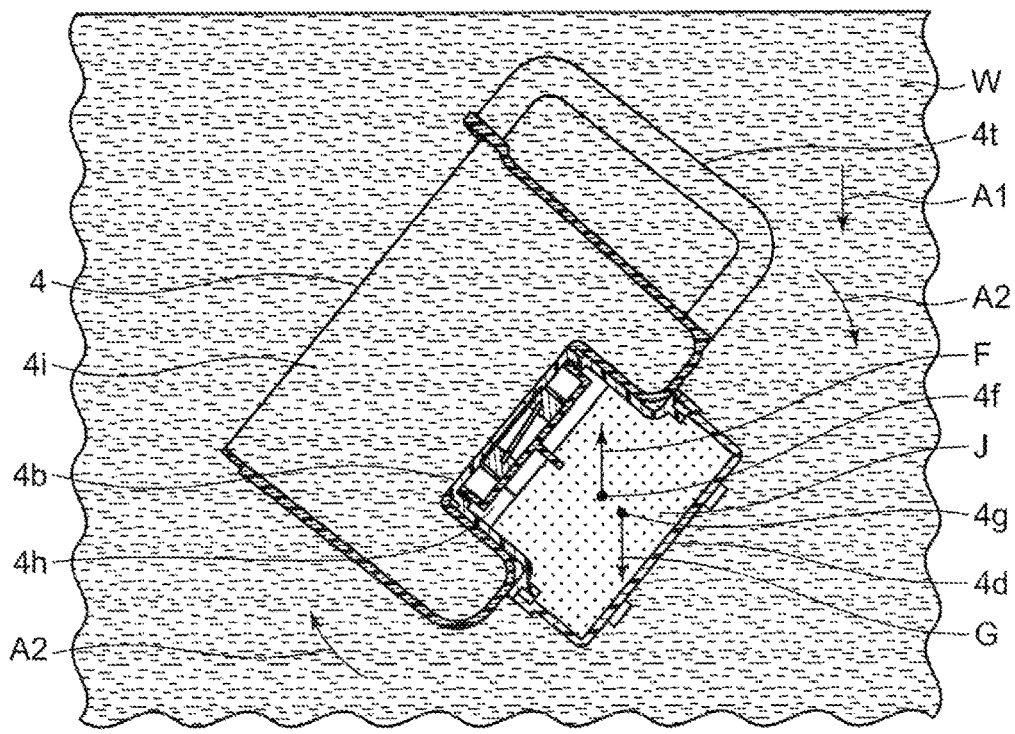
FIG. 11 is a diagram showing a process in which the working tank sinks in the disinfecting liquid.
Figure 12:
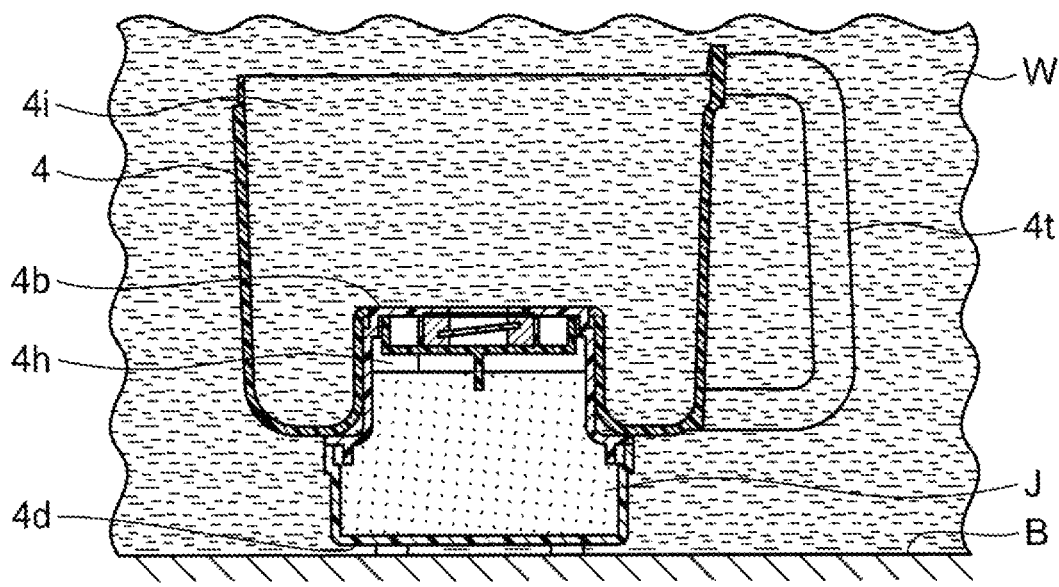
FIG. 12 is a diagram illustrating a mode in which the working tank has sunk in the disinfecting liquid.

Also, the center of gravity 4g of the working tank 4 is at a part that is closer to the outer bottom surface 4d than the center of buoyancy 4f is, which receives the buoyant force from the water or disinfecting liquid when the working tank 4 is immersed in the water or disinfecting liquid. Accordingly, as shown in FIG. 11, in the process of sinking in the disinfecting liquid W in the direction of the arrow A1, the working tank 4 uprights itself by receiving the rotational moment A2 caused by the buoyant force F received at the center of buoyancy 4f and the gravitational force G received at the center of gravity 4g. As a result, as shown in FIG. 12, the working tank 4 enters a state of being upright on the bottom surface B of the disinfecting liquid tank and is subjected to disinfection in a preferred state.

Figure 13:
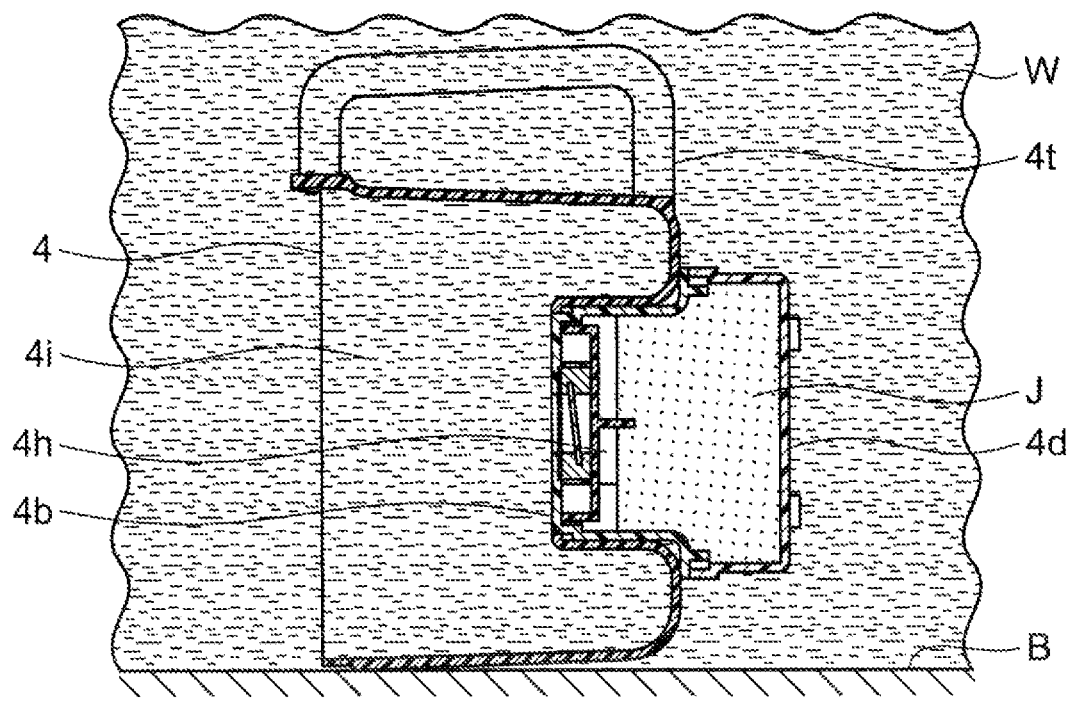
FIG. 13 is a diagram illustrating another mode in which the working tank has sunk in the disinfecting liquid.

Note that as shown in FIG. 13, even if the working tank 4 rolls sideways, if the working tank 4 is in a sunken state and no air remains in the tank inner space 4i, the working tank 4 is sufficiently subjected to disinfection.

In the above-described embodiment, a configuration was used in which mounting is performed by fitting the tank unit 3 (indicates the working tank 4 in particular; the same follows in this paragraph) on the main body 2 from above, and by contrast, removal is performed by pulling the tank unit 3 upward off of the main body 2. Accordingly, if the main body 2 is placed on a platform such as a desk, for example, and the user holds only the tank unit 3 with a hand and brings it close to the main body 2, mounting is easily performed. However, there is no limitation to this, and it is possible to use a configuration in which mounting is performed by bringing the tank unit 3 close to the main body 2 from rearward (or forward, or from the left), for example, and removal is performed by separating the tank unit 3 from the main body 2 in that direction. In other words, in the present invention, it is possible to use a configuration in which mounting is performed by bringing the tank unit close to the main body from a certain direction and removal is performed by separating the tank unit from the main body in that direction.

Also, in the above-described embodiment, as the weight, the sealing material J filled the gap 4h that forms the double-bottomed structure of the working tank 4. However, there is no limitation to this, and for example, a metal plate, for example, may be adhered as the weight to the lower portion of the working tank 4 using an adhesive, for example.

The above-described embodiment is merely an example and can be modified in various ways without departing from the scope of the invention. The various characteristics of the above-described embodiment can be realized independently, but it is also possible to combine the characteristics.

REFERENCE SIGNS LIST

1 Ultrasonic nebulizer
2 Main body
2u Containing portion
Tank unit
Working tank
Medicine tank support
6 Medicine tank
Medicine tank cover
Ultrasonic vibrator
J Sealing material

The invention claimed is:
1. An ultrasonic nebulizer comprising:
   a working tank in which an ultrasonic vibrator is incorporated and in which a working liquid is stored facing the ultrasonic vibrator;
   a medicine tank that stores a medicinal liquid, at least a bottom portion thereof being dipped in the working liquid; and
   a main body that includes an oscillation circuit that is to drive the ultrasonic vibrator,
   wherein the medicine tank is configured to be detachable with respect to the working tank,
   the working tank is configured to be detachable with respect to the main body,
   the working tank includes an approximately tube-shaped outer circumferential wall and an outer bottom surface that closes a lower portion of the outer circumferential wall,
   a bottom portion of the working tank has a double-bottomed structure that includes the outer bottom surface and an inner bottom surface that is provided on the outer bottom surface via a gap, and
   the working tank has a specific gravity that is larger overall compared to that of water or a disinfecting liquid and a weight is provided in the gap so that the working tank has a center of gravity at a part that is closer to the outer bottom surface than a center of buoyancy is, the center of buoyancy being a location at which a buoyant force is received from the water or the disinfecting liquid when the working tank is immersed in the water or the disinfecting liquid.
2. The ultrasonic nebulizer according to claim 1, wherein the weight is composed of a sealing material that fills the gap.
3. An ultrasonic nebulizer comprising:
   a working tank in which an ultrasonic vibrator is incorporated and in which a working liquid is stored facing the ultrasonic vibrator;

a medicine tank that stores a medicinal liquid, at least a bottom portion thereof being dipped in the working liquid; and a main body that includes an oscillation circuit that is to drive the ultrasonic vibrator, wherein the medicine tank is configured to be detachable with respect to the working tank, the working tank is configured to be mounted on the main body by being brought close thereto from above, and conversely, the working tank is removed from the main body by being separated therefrom in an upward direction, the main body includes a cylindrical containing portion that opens upward and surrounds and contains the mounted working tank and medicine tank, an opening that is continuous with the cylindrical containing portion is provided on a rear surface side of a main portion of the main body that surrounds the working tank and the medicine tank, a carrying handle is integrally attached to an outer circumferential wall of the working tank, and in a state in which the working tank is mounted on the main body, the handle is arranged at the opening that is continuous with the cylindrical containing portion of the main body.

4. The ultrasonic nebulizer according to claim 3, wherein a dimension in a left-right direction of the opening is set to be a dimension large enough for a first to be inserted therein.

5. The ultrasonic nebulizer according to claim 3, wherein in a state in which the working tank is mounted on the main body, a rear surface of the handle matches a rear surface of the main body.

6. The ultrasonic nebulizer according to claim 4, wherein in a state in which the working tank is mounted on the main body, a rear surface of the handle matches a rear surface of the main body.

* * * * *